(12) United States Patent
Krimsky

(10) Patent No.: US 11,471,217 B2
(45) Date of Patent: Oct. 18, 2022

(54) SYSTEMS, METHODS, AND COMPUTER-READABLE MEDIA FOR IMPROVED PREDICTIVE MODELING AND NAVIGATION

(71) Applicant: Covidien LP, Mansfield, MA (US)

(72) Inventor: William S. Krimsky, Forest Hill, MD (US)

(73) Assignee: COVIDIEN LP, Mansfield, MA (US)

(*) Notice: Subject to any disclaimer, the term of this patent is extended or adjusted under 35 U.S.C. 154(b) by 526 days.

(21) Appl. No.: 16/214,233

(22) Filed: Dec. 10, 2018

(65) Prior Publication Data
US 2019/0175276 A1 Jun. 13, 2019

Related U.S. Application Data

(60) Provisional application No. 62/597,233, filed on Dec. 11, 2017.

(51) Int. Cl.
*A61B 34/10* (2016.01)
*A61B 34/20* (2016.01)
(Continued)

(52) U.S. Cl.
CPC .............. *A61B 34/10* (2016.02); *A61B 5/062* (2013.01); *A61B 5/113* (2013.01); *A61B 5/1127* (2013.01);
(Continued)

(58) Field of Classification Search
CPC ......... A61B 5/113; A61B 34/10; A61B 34/20; A61B 5/062; A61B 5/7275; A61B 5/7475;
(Continued)

(56) References Cited

U.S. PATENT DOCUMENTS

| | | |
|---|---|---|
| 4,043,324 A | 8/1977 | Shaw, IV |
| 4,150,292 A | 4/1979 | Ter-Pogossian |
| | (Continued) | |

FOREIGN PATENT DOCUMENTS

| | | |
|---|---|---|
| WO | 0010456 A1 | 3/2000 |
| WO | 0167035 A1 | 9/2001 |
| | (Continued) | |

OTHER PUBLICATIONS

International Search Report and Written Opinion issued in corresponding Appl. No. PCT/US2018/064933 dated Jul. 4, 2019 (11 pages).

(Continued)

*Primary Examiner* — Amelie R Davis
*Assistant Examiner* — John Denny Li
(74) *Attorney, Agent, or Firm* — Carter, DeLuca & Farrell LLP

(57) ABSTRACT

Disclosed are systems, methods, and computer-readable media for navigating to and interacting with a region of interest during a respiratory cycle of a patient. An exemplary system includes a percutaneous tool, a plurality of patient sensors disposed on the patient, a tracking module configured to determine location and motion data of the plurality of patient sensors and a tool coupled to the percutaneous tool, a display device, and a computing device configured to receive a plurality of images of the patient's body, receive the location and motion data determined by the tracking module, generate a model of the interior of the patient, determine likely movement of the interior of the patient, the percutaneous tool, and the region of interest throughout the respiratory cycle, and cause the display device to display a graphical user interface including a window for depicting movement throughout the respiratory cycle.

19 Claims, 6 Drawing Sheets

(51) Int. Cl.
*A61B 5/00* (2006.01)
*A61B 5/06* (2006.01)
*A61B 5/113* (2006.01)
*A61B 5/11* (2006.01)
*A61B 10/02* (2006.01)

(52) U.S. Cl.
CPC .......... *A61B 5/7275* (2013.01); *A61B 5/7475* (2013.01); *A61B 34/20* (2016.02); *A61B 10/0233* (2013.01); *A61B 2034/102* (2016.02); *A61B 2034/105* (2016.02); *A61B 2034/107* (2016.02); *A61B 2034/2051* (2016.02)

(58) Field of Classification Search
CPC ........ A61B 2034/102; A61B 2034/105; A61B 2034/107; A61B 2034/2051; A61B 10/0233
See application file for complete search history.

(56) References Cited

U.S. PATENT DOCUMENTS

| | | | |
|---|---|---|---|
| 4,629,989 A | 12/1986 | Riehl et al. | |
| 5,090,401 A | 2/1992 | Schwieker | |
| 5,099,855 A | 3/1992 | Yount | |
| 5,784,431 A | 7/1998 | Kalend et al. | |
| 6,188,355 B1 | 2/2001 | Gilboa | |
| 6,279,579 B1 | 8/2001 | Riaziat et al. | |
| 6,292,682 B1 | 9/2001 | Kruger | |
| 6,374,667 B1 | 4/2002 | Eriksen et al. | |
| 6,731,970 B2 | 5/2004 | Schlossbauer et al. | |
| 7,154,991 B2 | 12/2006 | Earnst et al. | |
| 7,221,733 B1 | 5/2007 | Takai et al. | |
| 7,233,820 B2 | 6/2007 | Gilboa | |
| 8,042,209 B2 | 10/2011 | D'Souza et al. | |
| 8,821,376 B2 | 9/2014 | Tolkowsky | |
| 9,247,992 B2 | 2/2016 | Ladtkow et al. | |
| 9,459,770 B2 | 10/2016 | Baker | |
| 2005/0165324 A1 | 7/2005 | Receveur et al. | |
| 2005/0182295 A1 | 8/2005 | Soper et al. | |
| 2008/0221442 A1 | 9/2008 | Tolkowsky et al. | |
| 2011/0092793 A1* | 4/2011 | Thomson | A61N 5/1049 600/407 |
| 2011/0160569 A1 | 6/2011 | Cohen et al. | |
| 2013/0303876 A1 | 11/2013 | Gelfand et al. | |
| 2014/0177931 A1 | 6/2014 | Kocherscheidt et al. | |
| 2014/0270441 A1 | 9/2014 | Baker | |
| 2014/0282216 A1 | 9/2014 | Baker | |
| 2015/0141869 A1 | 5/2015 | Costello et al. | |
| 2015/0265257 A1 | 9/2015 | Costello et al. | |
| 2015/0305650 A1 | 10/2015 | Hunter et al. | |
| 2016/0000356 A1 | 1/2016 | Brown et al. | |
| 2016/0135664 A1 | 5/2016 | Jasperson et al. | |
| 2016/0166336 A1 | 6/2016 | Razzaque et al. | |
| 2016/0296193 A1* | 10/2016 | Hofmann | A61B 6/5288 |
| 2017/0156685 A1 | 6/2017 | Dickhans et al. | |
| 2017/0215969 A1* | 8/2017 | Zhai | G06T 7/248 |
| 2017/0251951 A1* | 9/2017 | Hunter | A61B 5/113 |
| 2017/0273635 A1* | 9/2017 | Li | A61B 5/113 |
| 2017/0294018 A1 | 10/2017 | Averbuch et al. | |
| 2017/0358095 A1* | 12/2017 | Levy | A61B 5/7292 |
| 2019/0051408 A1* | 2/2019 | Hanajima | A61B 90/98 |

FOREIGN PATENT DOCUMENTS

| | | |
|---|---|---|
| WO | 2015076936 A1 | 5/2015 |
| WO | 2015103061 A1 | 7/2015 |
| WO | 2015164587 A2 | 10/2015 |
| WO | 2016004177 A1 | 1/2016 |
| WO | 2016018648 A1 | 2/2016 |

OTHER PUBLICATIONS

International Search Report and Written Opinion for application No. PCT/US2017/045110 dated Nov. 14, 2017 (10 pages).
ISR for PCT/US06/13813, dated Oct. 2, 2006, D'Souza.
D'Souza et al., "Real-time intra-fraction-motion tracking using the treatment couch: a feasibility study," Physics Med. Biol. 50: 1-13 (2005), Abstract.
D'Souza et al., "An analysis of the treatment couch and control system dynamics for respiration-induced motion compensation," Am. Assoc. Phys. Med. 33(12): 4701-4709 (2006) Abstract.
European Search Report dated Jan. 19, 2018 issued in European Patent Application No. 17187480.3.

* cited by examiner

SYSTEMS, METHODS, AND COMPUTER-READABLE MEDIA FOR IMPROVED PREDICTIVE MODELING AND NAVIGATION

CROSS REFERENCE TO RELATED APPLICATION

The present application claims the benefit of and priority to U.S. Provisional Application Ser. No. 62/597,233, filed on Dec. 11, 2017 the entire contents of which are incorporated herein by reference.

BACKGROUND

Technical Field

The present disclosure relates to systems, methods, and computer-readable media for providing assistance during surgeries, and particularly, to enabling improved predictive models and navigation to a region of interest within a patient's body, such as areas at or near the thoracic cavity throughout the patient's respiratory cycle.

Description of Related Art

A needle biopsy procedure is a medical procedure used to obtain a tissue sample from an area of the body. The tissue sample may be tested to assist in diagnosing a medical condition or to assess the effectiveness of a particular treatment. Percutaneous needle lung biopsy or transthoracic needle lung biopsy involves the use of a needle to enter the lung through the skin or an airway, placing the needle at a region of interest within the body, and obtaining a biopsy sample at the region of interest. In order to properly perform a biopsy, it is important that the needle be placed at the desired region of interest within the body of the patient. However, during navigation of the needle to the region of interest, a patient continues their respiratory cycle, thereby causing movement of the region of interest and the tools used during the placement of the needle. It is difficult to assess locations of percutaneous tools and other diagnostic instruments with respect to these moving regions of interest during respiration. Thus, many clinicians rely on their experience and physiological understanding of movement to determine where the percutaneous tools and other diagnostic instruments should be located during such a procedure. Like all experience-based approaches, the outcomes can be mixed, and therefore improvements are needed.

SUMMARY

Provided in accordance with an embodiment of the present disclosure is a system for navigating to and interacting with a region of interest during a respiratory cycle of a patient. In an aspect of the present disclosure, the system includes a percutaneous tool including a tool sensor, the percutaneous tool configured for insertion into an interior of a patient and interaction with a region of interest during a surgical procedure, an electromagnetic (EM) tracking system including an EM field generator configured to generate an EM field, a plurality of patient sensors disposed on the patient and movable within the EM field, and a tracking module configured to determine location and motion data of the plurality of patient sensors and the tool sensor within the EM field. The system further includes a display device, and a computing device including at least one processor, and a memory storing instructions which, when executed by the at least one processor, cause the computing device to receive a plurality of images of the patient's body, receive the location and motion data determined by the tracking module, generate a three-dimensional (3D) model of at least a portion of the interior of the patient based on the plurality of images, determine likely movement of the interior of the patient, the percutaneous tool, and the region of interest throughout the respiratory cycle based on the location and motion data determined by the tracking module, and cause the display device to display a graphical user interface (GUI) including a window for depicting movement of the interior of the patient, the percutaneous tool, and the region of interest throughout the respiratory cycle.

In another aspect of the present disclosure, the respiratory cycle is divided into an inhalation phase and an exhalation phase, and each image of the plurality of images corresponds to either the inhalation phase or the exhalation phase.

In a further aspect of the present disclosure, the instructions, when executed by the at least one processor, further cause the computing device to determine likely movement of the interior of the patient and the region of interest throughout the respiratory cycle based on the location and motion data of the plurality of patient sensors and the 3D model of the interior of the patient.

In yet a further aspect of the present disclosure, the instructions, when executed by the at least one processor, further cause the computing device to determine likely movement of the percutaneous tool based on the determined likely movement of the interior of the patient and the location and motion data of the tool sensor.

In another aspect of the present disclosure, the GUI window includes a model window configured to display a view of the 3D model of the interior of the patient, the percutaneous tool, the region of interest, and the determined likely movement of the interior of the patient, the percutaneous tool, and the region of interest throughout the respiratory cycle.

In a further aspect of the present disclosure, the model window is further configured to display a trajectory of the percutaneous tool.

In yet a further aspect of the present disclosure, the model window is further configured to display a proposed trajectory of the percutaneous tool throughout the respiratory cycle, and a proposed location of the region of interest throughout the respiratory cycle.

In still a further aspect of the present disclosure, the proposed trajectory of the percutaneous tool and the proposed location of the region of interest change throughout the respiratory cycle.

In yet a further aspect of the present disclosure, the instructions, when executed by the at least one processor, further cause the computing device to determine interaction with the region of interest if the trajectory of the percutaneous tool is closely matched with the proposed trajectory of the percutaneous tool.

In still a further aspect of the present disclosure, the instructions, when executed by the at least one processor, further cause the computing device to determine interaction with the region of interest based on the trajectory of the percutaneous tool, the proposed trajectory of the percutaneous tool, and the proposed location of the region of interest.

In another aspect of the present disclosure, the GUI window includes a predictive window configured to display a plurality of predictive metrics.

In a further aspect of the present disclosure, the predictive metrics include one or more of patient chest motion during respiration, a distance of movement of the region of interest during respiration, and an indication of interaction with the region of interest.

In another aspect of the present disclosure, the GUI window includes an indicator window configured to display a tool indicator, a respiratory indicator, and a procedure indicator, and the tool indictor indicates the type of tool being used during the surgical procedure, the respiratory indicator indicates a phase of the respiratory cycle, and the procedure indicator indicates a type of the surgical procedure.

In another aspect of the present disclosure, the percutaneous tool is selected from the group consisting of an aspiration needle, an access tool, a biopsy tool, and an ablation tool.

Provided in accordance with an embodiment of the present disclosure is a method for navigating to and interacting with a region of interest during a respiratory cycle of a patient. In an aspect of the present disclosure, the method includes receiving a plurality of images of a patient's body, generating a three-dimensional (3D) model of at least a portion of an interior of the patient's body and a 3D model of a region of interest based on the plurality of images, detecting a position of a percutaneous tool inserted into the interior of the patient based on a tool sensor coupled to the percutaneous tool, obtaining location and motion data of the tool sensor and a plurality of sensors disposed on the patient within an electromagnetic (EM) field generated by an EM tracking system, determining likely movement of the interior of the patient, the percutaneous tool, and the region of interest, and displaying a graphical user interface (GUI), the GUI including a model window configured to display a view of the 3D model of the interior of the patient, the percutaneous tool, the region of interest, and the determined likely movement of the interior of the patient, the percutaneous tool, and the region of interest throughout the respiratory cycle.

In another aspect of the present disclosure, determining likely movement of the interior of the patient and the region of interest is based on the location and motion data of the plurality of sensors and the 3D model.

In yet another aspect of the present disclosure, the user interface further includes an indicator window configured to display a tool indictor, a respiratory indicator, and a procedure indicator, and the tool indictor indicates the type of tool being used during the surgical procedure, the respiratory cycle indicator indicates a position within the respiratory cycle, and the procedure indicator indicates a type of the surgical procedure.

In a further aspect of the present disclosure, the model window is further configured to display a trajectory of the percutaneous tool, a proposed trajectory of the percutaneous tool throughout the respiratory cycle, and a proposed location of the region of interest throughout the respiratory cycle.

In yet a further aspect of the present disclosure, the proposed trajectory of the percutaneous tool and the proposed location of the region of interest change throughout the respiratory cycle.

In still a further aspect of the present disclosure, the method further includes determining interaction with the region of interest if the trajectory of the percutaneous tool is closely matched with the proposed trajectory of the percutaneous tool.

In yet a further aspect of the present disclosure, the method further includes determining interaction with the region of interest based on the trajectory of the percutaneous tool, the proposed trajectory of the percutaneous tool, and the proposed location of the region of interest.

Any of the above aspects and embodiments of the present disclosure may be combined without departing from the scope of the present disclosure.

BRIEF DESCRIPTION OF THE DRAWINGS

Objects and features of the presently disclosed system, methods, and computer readable media will become apparent to those of ordinary skill in the art when descriptions of various embodiments thereof are read with reference to the accompanying drawings, wherein.

DETAILED DESCRIPTION

Figure 1:
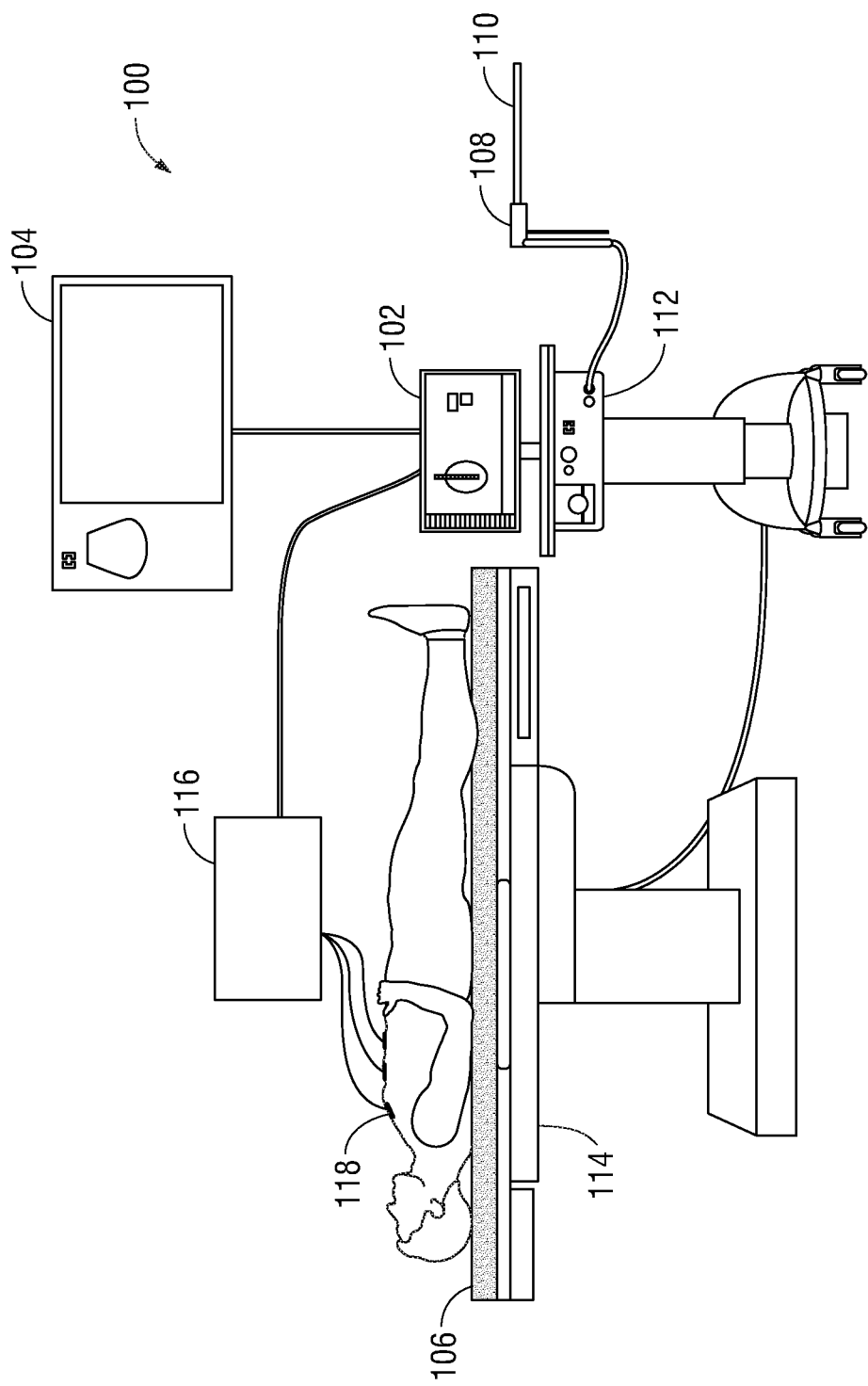
FIG. 1 is a perspective view of a surgical system in accordance with the present disclosure.

Provided in accordance with the present disclosure are systems, methods, and computer-readable media for generating improved predictive models and guidance during navigation of medical tools to a region of interest within a patient's body, and more specifically, to areas at or near the thoracic cavity throughout the patient's respiratory cycle. Prior to performing various medical procedures as described herein, a computing device, such as computing device 102 shown in FIG. 1, may utilize radiographic image data, such as computed tomography (CT) image data, magnetic resonance imaging (MRI) image data, positron emission tomography (PET) image data, X-ray image data, cone-beam computed tomography (CBCT) image data, or fluoroscopic image data, as well as ultrasound image data and/or any other image data stored in a standardized image format, such as the Digital Imaging and Communications in Medicine (DICOM) format or any other relevant imaging format, for generating and viewing a three-dimensional (3D) model of at least a portion of the patient's body. The 3D model, and images derived from the 3D model, enables the identification of the region of interest (automatically, semi-automatically or manually), and allows for the selection of a specific path to the region of interest. More specifically, data acquired by radiographic or other forms of imaging during a scan of one or more portions of the patient's body is processed and assembled into a 3D volume, which is then utilized to generate the 3D model of at least a portion of the patient's body. The 3D model may be displayed on one or more display devices, such as the display 104 (FIG. 1) and/or the display 204 (FIG. 2), as further described below. While those skilled in the art will recognize that any of the above-described radiographic or ultrasound imaging modalities and/or various combinations thereof may be used during the procedures described hereinbelow, CT will be used as an illustrative imaging modality in the examples described below. However, the use of CT as an illustrative imaging modality is not intended to be limiting, and any other application imaging modality may be substituted for CT and/or used in addition to CT without departing from the scope of the present disclosure.

Generally, during imaging of a patient to obtain CT image data, the patient's breath is held at a particular point in the patient's respiratory cycle to generate a single set of image slices based on either the maximum inhalation point or maximum exhalation point of the respiratory cycle. It is also understood that the respiratory cycle is composed of various transition points or phases between the maximum inhalation point and the maximum exhalation point. As used herein, the maximum inhalation point refers to the peak or near-peak expansion of the patient's chest cavity as the lungs fill with air during tidal volume breathing, while the maximum exhalation point refers to the peak or near-peak contraction of the patient's chest cavity due to expiration of air from the patient's lungs during tidal volume breathing. Each of the maximum inhalation point and the maximum exhalation point refer to the maximum inhalation and exhalation, respectively, of patient breathing, while normal tidal volume breathing occurs between the maximum inhalation point and the maximum exhalation point. Those skilled in the art will recognize that the maximum inhalation point and maximum exhalation point during tidal volume breathing may not be the absolute maximum inhalation and absolute maximum exhalation points, respectively, since the patient may not fully inhale and/or fully exhale to the absolute maximum inhalation and/or exhalation points, respectively.

By tracking positions of one or more position sensors 118 (shown in FIG. 1), and determining their positions in an electromagnetic (EM) field at the maximum inhalation point and the maximum exhalation point, these positions may be correlated to the CT image data, taken at full breath hold. By tracking the changes in the location of the sensors 118, and applying an appropriate algorithm, a determination may be made as to how the CT image data, and thus the 3D model, should be adjusted to depict movement of a region of interest and how the locations of organs and other physiological structures change throughout the patient's respiratory cycle. This can be particularly useful in displaying the differences in expected location of the region of interest at full breath hold as compared to during normal tidal volume breathing. Another factor that substantially affects the locations of organs and other physiological structures, as well as the patient's respiratory cycle itself, is the position of the patient on an operating table, such as table 114 of FIG. 1, described below. For example, if the patient is positioned in a prone position (i.e. face down on table 114), movement of the patient's chest may be restricted, while if the patient is positioned face up, more normal respiration movement may be observed. As such, the determination as to how to adjust the 3D model throughout the respiratory cycle to depict movement of the region of interest and how the locations of organs and other physiological structures change may further be based on the position of the patient on table 114.

Referring now to FIG. 1, there is shown a percutaneous diagnostic and treatment system 100, in accordance with embodiments of the present disclosure. System 100 includes the computing device 102, the display 104, a percutaneous tool 108 including an EM sensor 110, and table 114. Also shown in FIG. 1 is an electrosurgical generator 112, which forms part of an integrated navigation and treatment system that may be interconnected with and/or controlled by the computing device 102. In other embodiments, the electrosurgical generator 112 may be a standalone generator coupled with the computing device 102.

The percutaneous tool 108 may be an aspiration needle, an access tool, a biopsy tool, an ablation tool, temperature sensor, and/or any other surgical tool or combination of tools that may be used during a percutaneous surgical procedure. The computing device 102 may be, for example, a laptop computer, desktop computer, tablet computer, or other similar device. The computing device 102 may be configured to control the electrosurgical generator 112, a peristaltic pump (not shown), a power supply (not shown), and/or any other accessories and peripheral devices relating to, or forming part of, the system 100. The display 104 is configured to receive and display instructions, images, and/or messages relating to the performance of the surgical procedure.

The table 114 may be, for example, an operating table or other table suitable for use during a surgical procedure, which includes an EM field generator 106. The EM field generator 106 is used to generate an EM field during the procedure and forms part of an EM tracking system 116, which is used to track the positions of sensors, such as EM sensor 110, on surgical instruments within the patient's body, and sensors, such as the reference sensors 118, on the patient's body. In some embodiments, the percutaneous tool 108 is a percutaneous needle biopsy tool capable of being inserted into a patient and obtaining tissue samples. In other embodiments, the percutaneous tool 108 may be a microwave ablation antenna that is used to ablate tissue. In addition to the EM tracking system 116, the surgical instruments utilized with the system 100 may also be visualized by using imaging techniques, such as an ultrasound imager (not shown), fluoroscopic imager (not shown), CBCT imager (not shown), and/or the like.

As described herein, the percutaneous tool 108 may be used to obtain a tissue sample of a lesion or tumor (hereinafter referred to as a "region of interest" or a "target") or to treat tissue at the region of interest by using energy, such as electromagnetic, radiation, and/or microwave energy, to heat tissue in order to denature or kill cancerous cells. The construction and use of an ablation system usable with percutaneous tools, such as the percutaneous tool 108, is more fully described in co-pending U.S. Patent Appl. Publ. No. 2016/0058507, entitled MICROWAVE ABLATION SYSTEM, filed on Aug. 26, 2014, by Dickhans, co-pending U.S. Patent Appl. Publ. No. 2014/0046315, entitled MICROWAVE ABLATION CATHETER AND METHOD OF UTILIZING THE SAME, filed on Mar. 15, 2013, by Ladtkow et al., and co-pending U.S. Patent Appl. Publ. No. 2014/0276739, entitled MICROWAVE ENERGY-DELIVERY DEVICE AND SYSTEM, filed on Mar. 15, 2013, by Brannan et al., the entire contents of each of which are hereby incorporated by reference.

The location of the percutaneous tool 108, once inserted into the patient's body, may be tracked during the surgical procedure. The location of the percutaneous tool 108 may be determined through the use of the EM tracking system 116, which tracks the location of the percutaneous tool 108 by tracking EM sensor 110 coupled to and/or incorporated in the percutaneous tool 108. Various types of sensors may be used, such as a printed sensor, the construction and use of which is more fully described in co-pending U.S. Patent Appl. Publ. No. 2016/0174873, filed Oct. 10, 2015, titled MEDICAL INSTRUMENT WITH SENSOR FOR USE IN A SYSTEM AND METHOD FOR ELECTROMAGNETIC NAVIGATION, by Greenberg et al., the entire contents of which are incorporated herein by reference. Prior to starting the surgical procedure, the clinician is able to verify the accuracy of the tracking system.

Figure 2:
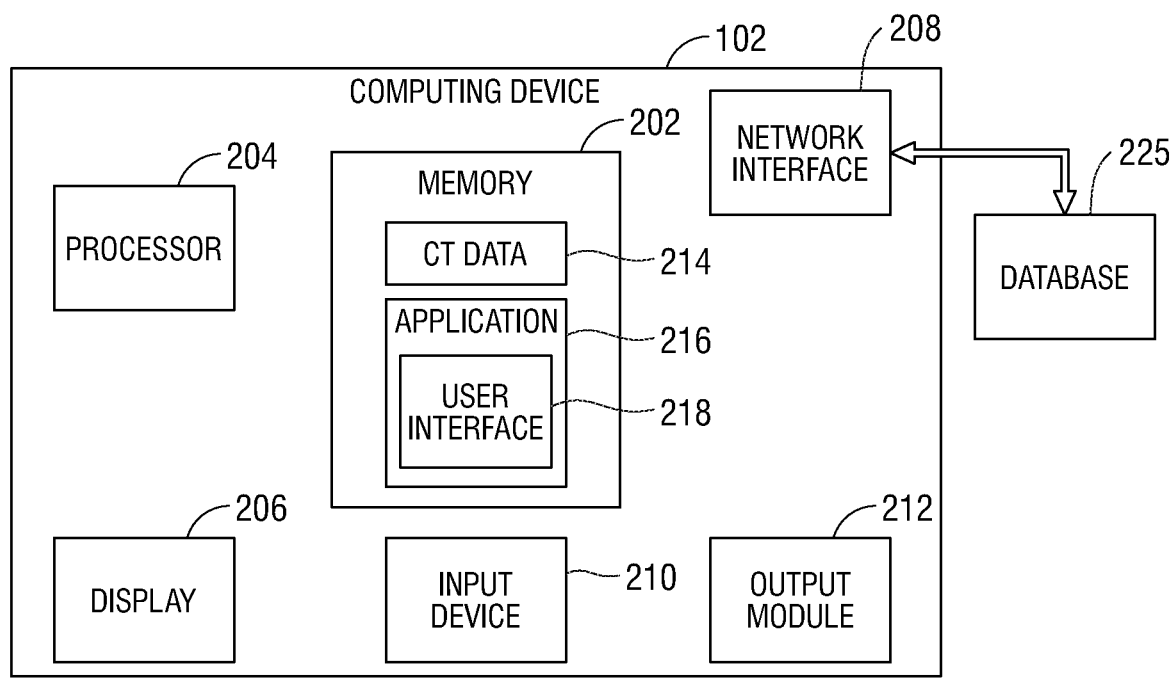
FIG. 2 is a schematic diagram of a workstation configured for use with the system of FIG. 1, in accordance with the present disclosure.

Turning now to FIG. 2, there is shown a schematic diagram of the computing device 102. The computing device 102 may include a memory 202, a processor 204, the display 206, a network interface 208, an input device 210, and/or an output module 212. Computing device 102 may further be connected to a database 225, such as via the network interface 208. The memory 202 includes any non-transitory computer-readable storage media for storing data and/or software that is executable by the processor 204 and which controls the operation of the computing device 102 and may store an application 216 and/or CT data 214. The application 216 includes instructions which, when executed by the processor 204, may cause the display 206 to present a user interface, such as generated via user interface module 218. The network interface 208 may be configured to connect to a network such as a local area network (LAN) consisting of a wired network and/or a wireless network, a wide area network (WAN), a wireless mobile network, a Bluetooth network, and/or the internet. The input device 210 may be any device by means of which a user may interact with the computing device 102, such as, for example, a mouse, keyboard, foot pedal, touch screen, voice interface, and/or computer-vision interface. The output module 212 may include any connectivity port or bus, such as, for example, parallel ports, serial ports, universal serial busses (USB), or any other similar connectivity port known to those skilled in the art. The database 225 includes patient metrics including, but not limited to, patient name, patient statistics (e.g., age, weight, height, etc.), patient health data (e.g., known respiratory and other health conditions), previous surgical procedures performed on the patient, and the like.

Figure 3:
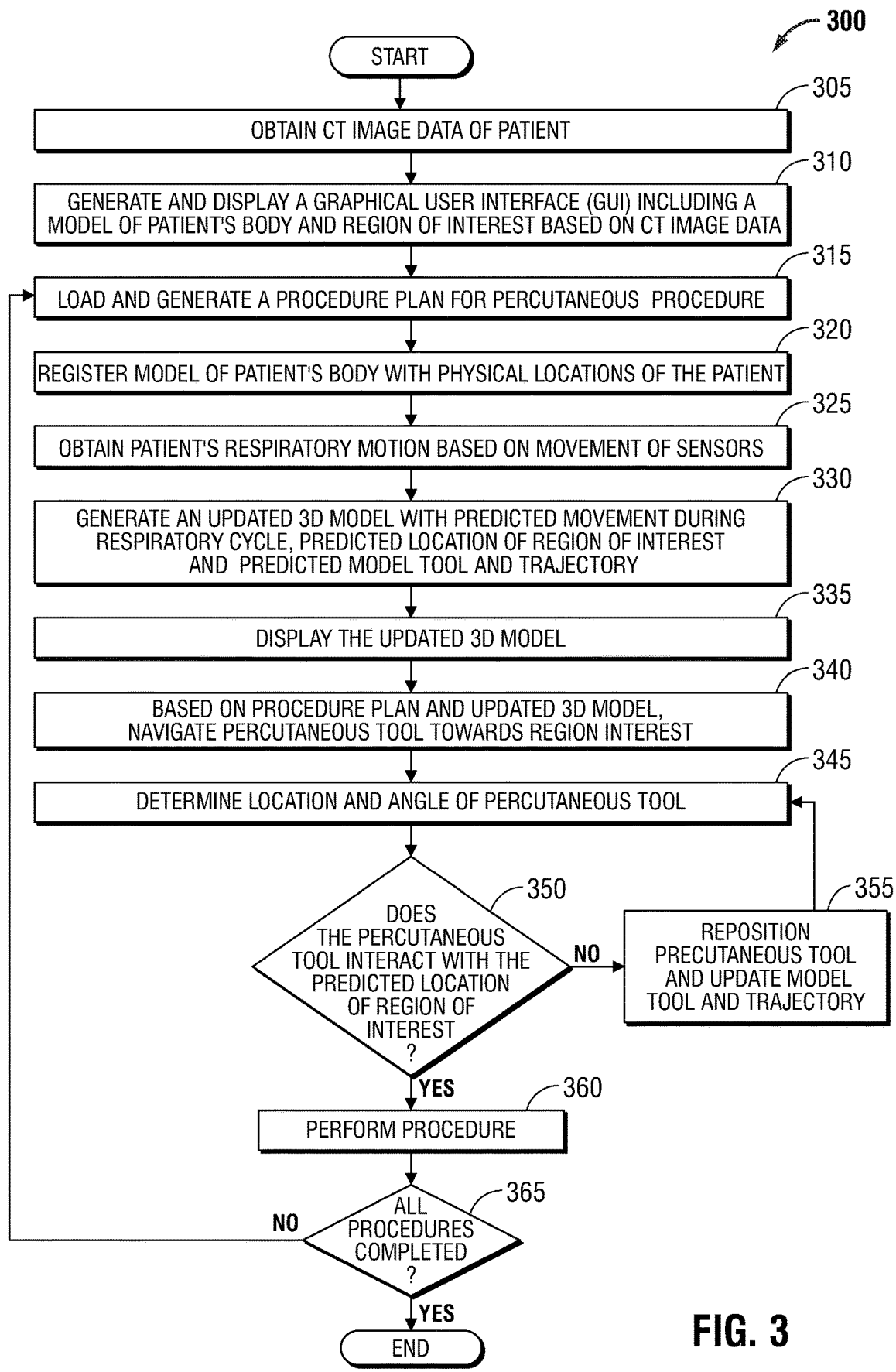
FIG. 3 is a flowchart illustrating a method for navigating to the location of and interacting with a region of interest during respiration, in accordance with the present disclosure.

Referring now to FIG. 3, there is shown a flowchart of an example method 300 for navigating to a region of interest during a surgical procedure, in accordance with embodiments of the present disclosure. Method 300 begins at step 305 where the computing device 102 obtains CT image data of the patient taken during a CT scan. The CT image data may be locally stored in memory 202 in the computing device 102 or may be obtained via the network interface 208, a USB or other external storage device, etc. Next, at step 310, the computing device 102 causes the application 216 to generate a GUI and a 3D model based on the obtained CT image data, such as GUI 400 and 3D model 412, respectively (shown in FIGS. 4A-4C).

Next, at step 315, the computing device 102 loads a procedure plan including a planned insertion pathway to an identified region of interest into the application 216. The region of interest may be displayed on, or as part of, 3D model 412, such as by a region of interest indicator 416 (shown in FIG. 4A). A navigation application similar to the application 216 described herein is more fully described in commonly-owned U.S. Patent Appl. Publ. No. 2016/0038248, entitled TREATMENT PROCEDURE PLANNING SYSTEM AND METHOD, filed on Aug. 10, 2015, by Bharadwaj et al., the entire contents of which are incorporated herein by reference.

Next, at step 320, using features enabled through the GUI 400, the 3D model 412 is registered with the patient's body. This registration is required because the CT scan data may have been acquired while the patient was positioned in a manner that does not reflect the position of the patient during the surgical procedure, and therefore the positions of organs and/or other physiological structures inside the patient's body may differ. For example, the patient will typically lie on his or her back when the CT scan data is acquired, while, during the surgical procedure, the patient may be positioned in a different position, such as face down, on his or her side, or in some other position that is different from the position the patient was in when the CT scan data was acquired. The registration may be performed by placing EM sensor 110 associated with the percutaneous tool 108 at various locations, such as landmarks, on the patient that are also visible in the CT images. Examples of such locations include various ribs that terminate at a specific location and can be contacted by the percutaneous tool 108, the xiphoid process, the collarbones, etc. This can be a manual process, whereby the clinician places the percutaneous tool 108 with EM sensor 110 at these locations and then interacts with the application 216 to identify the detected location as corresponding with a desired location in the 3D model 412. Alternatively, the data can be automatically gathered by dragging the percutaneous tool 108 with EM sensor 110 along a pathway outlining the desired portion of the patient.

These positions where EM sensor 110 is placed proximate landmarks on the patient's body may be captured and displayed, whereafter the clinician may manually adjust the displayed traced outline to fit the 3D model 412 and confirm registration. Once sufficient data has been acquired by identifying detected physical locations with corresponding locations in the 3D model 412, registration may be accomplished via a variety of registration algorithms. Examples of such registration algorithms are more fully described in commonly-owned U.S. Patent Appl. Publ. No. 2011/0085720, entitled AUTOMATIC REGISTRATION TECHNIQUE, filed on May 14, 2010, by Barak et al., and U.S. Patent Appl. Publ. No. 2016/0000356, entitled REAL-TIME AUTOMATIC REGISTRATION FEEDBACK, filed on Jul. 2, 2015, by Brown et al., the entire contents of each of which are incorporated herein by reference. While the registration process focuses on aligning the patient's body with the 3D model, registration also ensures that the position of airways, vascular structures, pleura, and fissures of the lungs, as well as other organs and/or structures within the patient's body, are accurately determined. Registration of the 3D model to the patient's body may also be performed by acquiring intra-procedural image data of the patient while the patient is lying on table 114. Such intra-procedural image data may then be dynamically and/or automatically registered to the patient's body by aligning landmarks and/or fiducial markers in the image data with the corresponding structures in the patient's body because the patient's body would be substantially unchanged from when the intra-procedural image data was acquired. Such an automatic registration process based on intra-procedurally obtained image data is further described in commonly-owned U.S. Provisional Patent Appl. No. 62/462,171, entitled INTEGRATION OF MULTIPLE DATA SOURCES FOR LOCALIZATION AND NAVIGATION, filed on Feb. 22, 2017, by William S. Krimsky, the entire contents of which are incorporated herein by reference. Additional or alternative methods of patient-to-model registration may also be performed without departing from the scope of the present disclosure.

Next, at step 325, the computing device 102, based on data received from the reference sensors 118, determines movement of the patient's chest at the locations of the reference sensors 118. In addition, the clinician may ask the patient to go to maximum inhale and maximum exhale at some point before the inducement of any anesthesia or ventilation, as is common in such procedures. Data collected during such procedures can then be compared to image data from the CT scan to identify the detected locations that correspond to the image data at, for example, maximum inhalation. With these locations identified, the movement of the patient's chest can be monitored and a predictive model created which can be used to determine that a detected movement of a particular amount or percentage by any one of the reference sensors 118 in any given direction corresponds to an amount or percentage change of tissue (e.g., the lungs) at a measured distance from any one of the reference sensors 118. This results in a determination of likely movement of tissue and/or other biological material, as well as the region of interest 416, during patient respiration. Further details regarding monitoring of the movement of the patient's chest and generating predictive models of movement of structures within the patient's chest based on the patient's respiratory cycle are described in commonly-owned U.S. Patent Application No. 62/597,200, entitled SYSTEMS, METHODS, AND COMPUTER-READABLE MEDIA OF ESTIMATING THORACIC CAVITY MOVEMENT DURING RESPIRATION, filed on Dec. 11, 2017, by William S. Krimsky, the entire contents of which are incorporated herein by reference.

Figure 4A:
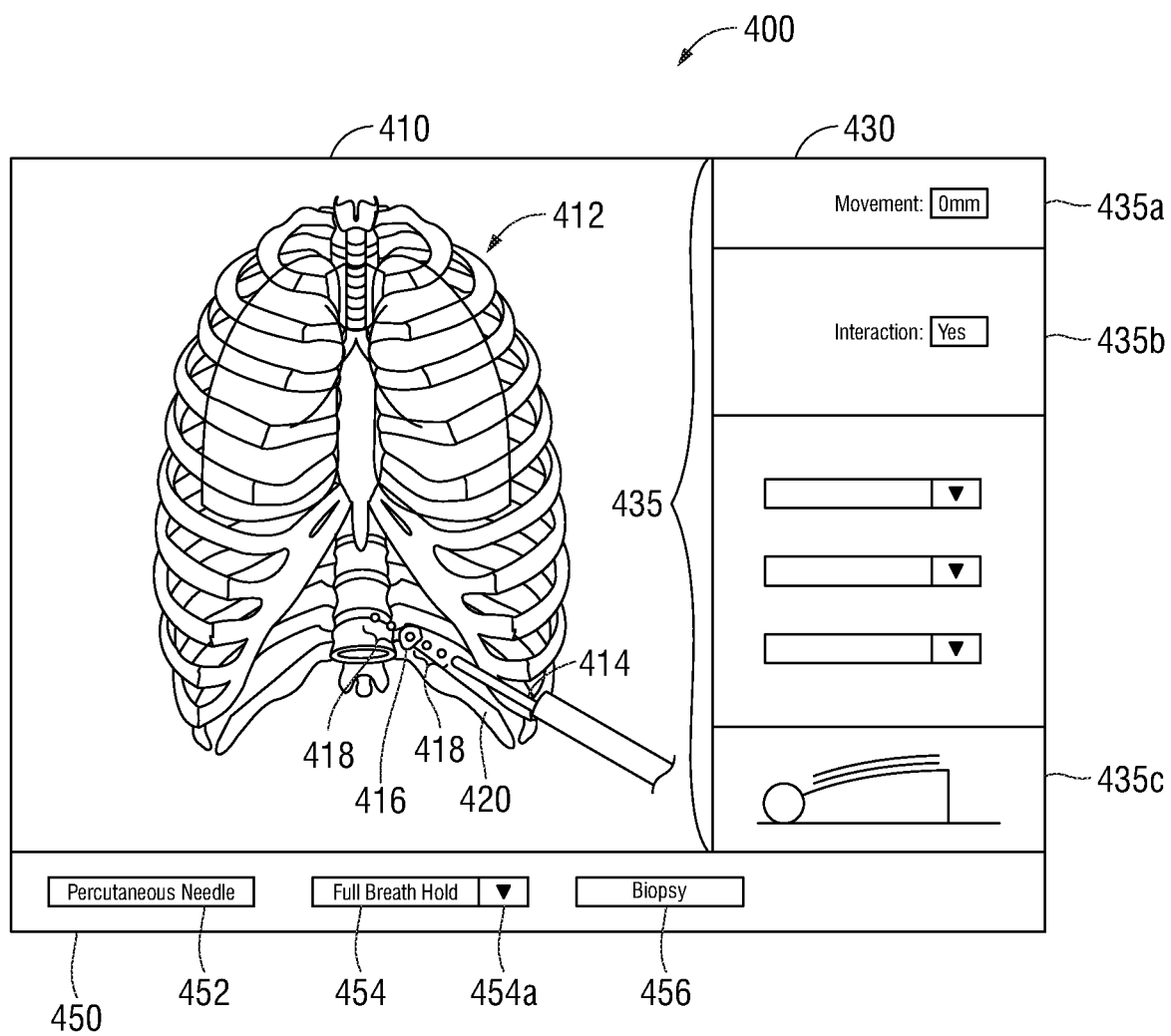
FIG. 4A-4C illustrate examples of a graphical user interface (GUI) window, in accordance with the present disclosure.
Figure 4B:
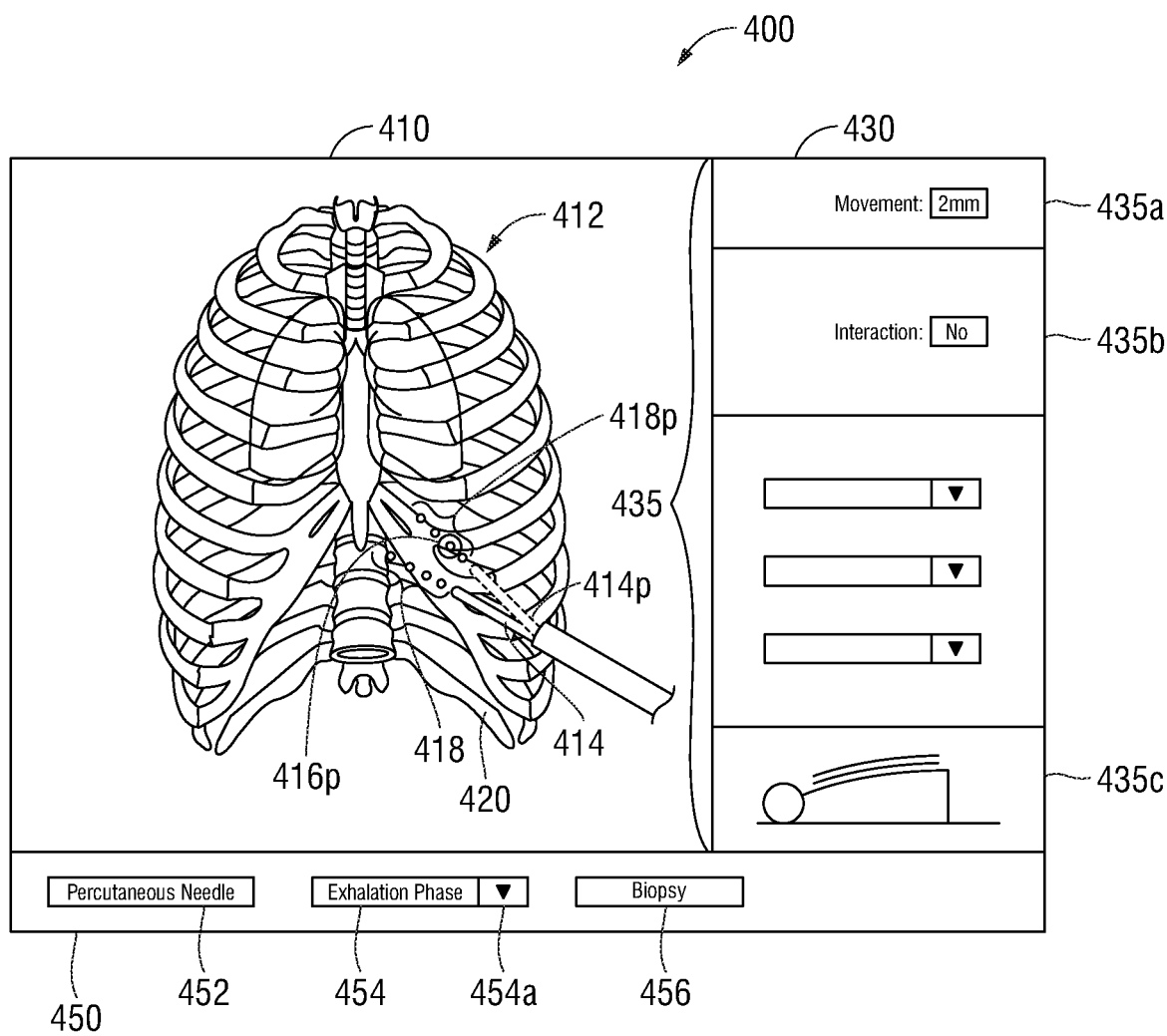
Figure 4C:
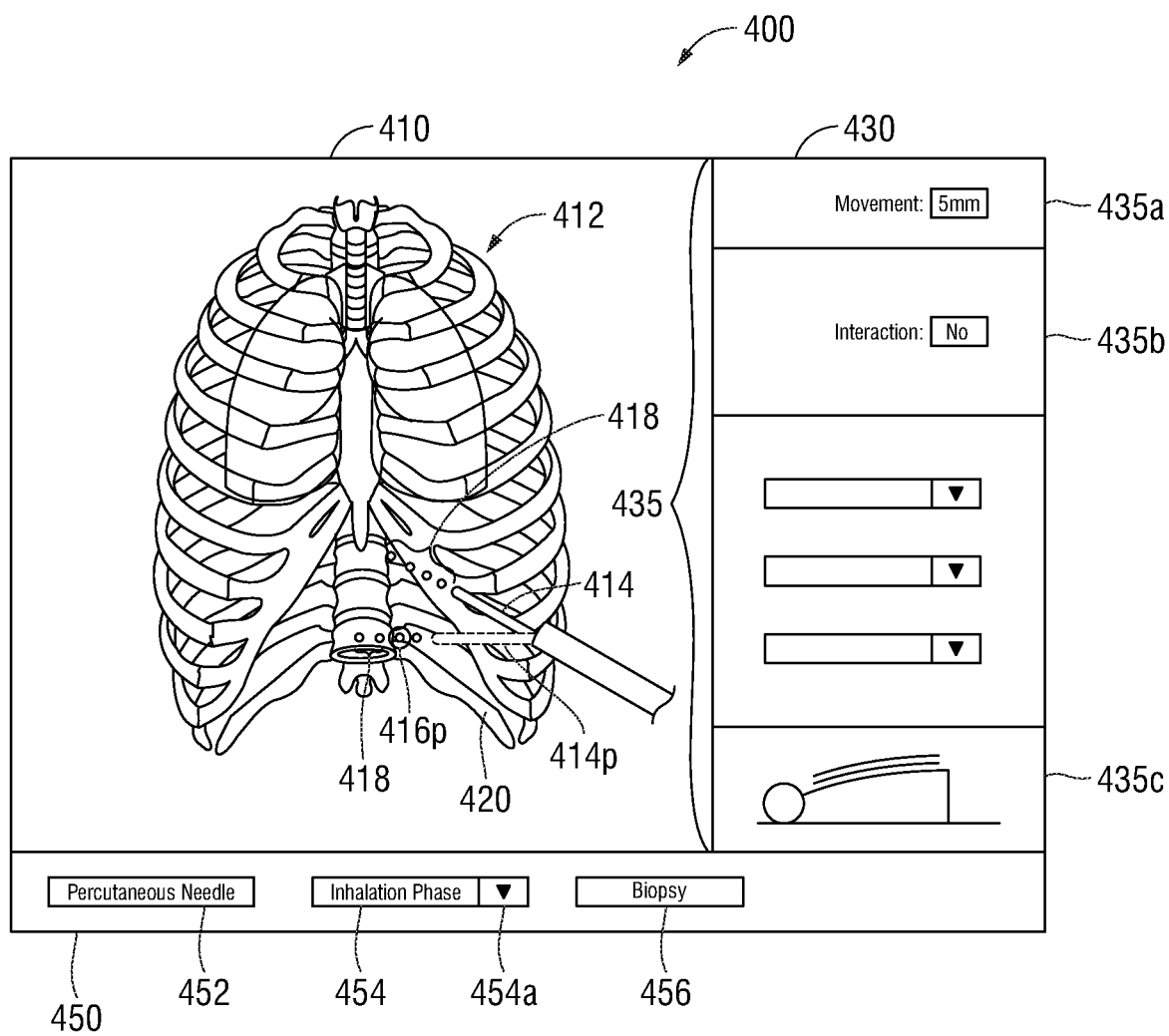

Next, at step 330, the movement of the reference sensors 118 is used to generate an updated version of the 3D model 412 that accounts for respiration of the patient, as shown in FIGS. 4B and 4C. The updated 3D model 412 may be displayed in the GUI 400 and includes a proposed location of the region of interest indicator 416$p$ throughout the respiratory cycle, a proposed tool position indicator 414$p$, and a proposed trajectory indicator 418$p$. In some embodiments, the proposed trajectory indicator 418$p$ is shown relative to the proposed location of the region of interest indicator 416$p$ and/or the region of interest indicator 416. As further described in the descriptions of FIGS. 4A-4C, the proposed tool position indicator 414$p$, and the proposed trajectory indicator 418$p$ provide graphical representations of locations to which a clinician should move the percutaneous tool 108 throughout the respiratory cycle in order to better ensure interaction with the region of interest 416. As such, the displayed proposed location of region of interest indicator 416$p$, the proposed trajectory indicator 418$p$, and/or the proposed tool position indicator 414$p$ may change throughout the respiratory cycle based on the movement of the reference sensors 118. Information from the database 225 may be utilized to supplement a predictive model for motion of the patient throughout the respiratory cycle based on the movement of the reference sensors 118. Next, at step 335, updated versions of the 3D model 412 are displayed throughout the respiratory cycle.

Thereafter, at step 340, based on the procedure plan and the updated 3D model 412, a clinician may navigate the percutaneous tool 108 towards the region of interest, as shown by region of interest indicator 416 in the updated 3D model 412. At step 345, using data received from EM sensor 110, the location and angle of the percutaneous tool 108 is determined. Next, at step 350, based on the determined location and angle of the percutaneous tool 108, a determination may be made as to whether the percutaneous tool 108 will interact with the proposed location of the region of interest 416$p$, the likely location of the region of interest during the current phase of the patient's respiratory cycle, as further detailed in the descriptions of FIGS. 4A-4C. If a tool position indicator 414 (a computer-generated model of the percutaneous tool 108 corresponding to the detected position and angle of the percutaneous tool within the patient's body, as further described with reference to FIGS. 4A-4C below) a virtual trajectory indicator 418 of percutaneous tool 108 is shown as interacting with the proposed location of the region of interest indicator 416$p$, an interaction metric 435$b$ (FIGS. 4A-4C) displays "YES," and method 300 proceeds to step 360, where the surgical procedure may be performed. Next, at step 365, a determination is made as to whether all surgical procedures have been completed. If all surgical procedures have been completed, method 300 ends. Alternatively, if it is determined at step 365 that additional surgical procedures are required, method 300 returns to step 315 where another surgical procedure plan is loaded.

If it is determined, at step 350, that the percutaneous tool 108 will not interact with the region of interest, and thus the tool position indicator 414 and/or the virtual trajectory indicator 418 is not shown as interacting with the proposed location of the region of interest indicator 416$p$, the interaction metric 335$b$ displays "NO," as shown in FIGS. 4B and 4C, and method 300 proceeds to step 355, where a clinician may reposition the percutaneous tool 108, thus causing the tool position indicator 414 and the trajectory indicator 418 to be updated. As described in the description of FIGS. 4B and 4C, if the percutaneous tool 108 is repositioned such that the tool position indicator 414 and the trajectory indicator 418 overlay the proposed tool position indicator 414$p$ and the proposed trajectory indicator 418$p$ (FIGS. 4A-4C), GUI 400 may show interaction with the proposed location of the region of interest indicator 416$p$, and a clinician may better predict that the percutaneous tool 108 is capable of performing the desired surgical procedure. Next, following step 355, method 300 returns to step 345.

Referring now to FIGS. 4A-4C, three illustrations of an example GUI 400 is shown. The GUI 400 may be displayed by the computing device 102, such as via the display 104 and/or the display 206. The GUI 400 includes a model window 410, a predictive window 430, and an indicator window 450. As shown in FIGS. 4A-4C, the model window 410 is illustrated as a window including graphical representations of the 3D model 412 of the interior of the patient, the tool position indicator 414, the region of interest indicator 416, the trajectory indicator 418, and tissue and/or other biological material 420. The model window 410 may further include a visual representation of the likely movement of the 3D model 412, the tool position indicator 414, the region of interest indicator 416, the trajectory indicator 418, and/or tissue and/or other biological material 420 throughout the patient's respiratory cycle. In some embodiments, the model window 410 may further include a visual representation of changes in the patient's respiratory cycle, alterations in the positions of various parts of the lung parenchyma as a consequence of positioning of the patient and/or atelectasis during the procedure. For example, depending on the positioning of the patient (e.g. face up, face down, on the side, etc.), the patient's respiratory cycle may be affected, and the visual representation of the likely movement of the aforementioned elements included in the model window 410 may be based on the positioning of the patient and may be different depending on the positioning of the patient.

The 3D model 412 is configured to show changes to the locations of the tool position indicator 414, the region of interest indicator 416, and the trajectory indicator 418 throughout the patient's respiratory cycle. The 3D model 412 may provide static images or dynamic (video) images depicting the change in locations or movement of features during the patient's respiratory cycle. It is contemplated that the 3D model 412 may be rotated, zoomed, and/or altered by a clinician to provide a better understanding of the locations of the tool position indicator 414 (and thus the percutaneous tool 108), the region of interest indicator 416, and the trajectory indicator 418. For example, where necessary, a clinician may remove some or all tissue, organs, and/or bones from the 3D model 412 in order to better view the tool position indicator 414, the region of interest indicator 416, and/or the trajectory indicator 418. Although the 3D model 412 is illustrated as a thoracic cavity, it is contemplated that other areas of the body that may be affected by respiration may also be imaged and utilized without departing from the scope of the present disclosure.

The tool position indicator 414 is illustrated as a 3D model of a cylindrical percutaneous needle biopsy tool, such as the percutaneous tool 108, extending into the 3D model 412. In embodiments where alternative percutaneous tools are utilized, the shape and configuration of the tool position indicator 414 are altered to detail a graphical model of the percutaneous tool utilized during the surgical procedure. The region of interest indicator 416 is illustrated as an oblong shaped mass intersected by the trajectory indicator 418. The shape, size, and configuration of the region of interest indicator 416 is based on the type of tissue and/or other biological material 420 that is being modeled within the model window 410.

The trajectory indicator 418 is illustrated as circles or dots extending beyond the distal end of the tool position indicator 414, and shows the trajectory at which the percutaneous tool 108 is being navigated inside the patient's body. The length of the trajectory 418 corresponds to the length of the percutaneous tool 108 and the size of the circles or dots of trajectory 418 corresponds to the width of the percutaneous tool 108. Thus, when positioning the percutaneous tool 108 outside the patient's body, the trajectory indicator 418 will show the distance that the percutaneous tool 108 can be navigated into the patient's body. As such, the clinician can determine whether the percutaneous tool 108 can reach the region of interest, as shown by the region of interest indicator 416, inside the patient's body before inserting the percutaneous tool 108 into the patient's body.

The predictive window 430 is illustrated as a window including graphical representations of a plurality of predictive metrics 435 that allow a clinician to better determine motion of the patient and the region of interest during respiration. The predictive metrics 435 may include, for example, a movement distance metric 435a, the interaction metric 435b, and/or a patient chest motion model 435c.

The movement distance metric 435a is an estimate of the predicted total distance between the region of interest indicator 416 and the distal-most tip of the tool position indicator 414 (and thus the percutaneous tool 108), based on the determination of the movement of the reference sensors 118, the distance of the region of interest indicator 416 from the reference sensors 118, and the location of EM sensor 110. For example, as shown in FIG. 4B, the movement distance metric 435a is displayed as 2 millimeters (mm), thereby informing a clinician that the distance between the region of interest indicator 416 and the distal-most tip of the tool position indicator 414 (and thus percutaneous tool 108) at the exhalation portion of the respiratory cycle is 2 mm. During respiration, the value of the movement distance metric 435a changes based on changes in respiratory motion of the patient, likely movement of the region of interest (as shown by the region of interest indicator 416), and the location of EM sensor 110. Thus, where the clinician maintains the location of the percutaneous tool 108 at the region of interest, the movement distance metric 435a will transition between maximum distances from the region of interest and 0 mm, as the region of interest and the percutaneous tool 108 move during respiration.

The interaction metric 435b is data of whether, based on the current location and insertion angle of the percutaneous tool 108, the tool position indicator 414 (representing the position of percutaneous tool 108) is capable of interacting with the region of interest indicator 416. Depending on the location and angle of the percutaneous tool 108, the tool position indicator 414 and the trajectory indicator 418 are updated along with the interaction metric 435b. As shown in the model window 410 of FIG. 4A, the trajectory indicator 418 intersects the region of interest indicator 416 and continues to extend beyond the region of interest indicator 416. Therefore, the interaction metric 435b is "YES." Although shown as the word "YES," in some embodiments, the interaction metric 435b may be various colors, shapes, text, or objects which indicate to a clinician whether the percutaneous tool 108 is capable of interacting with the region of interest. For example, the interaction metric 435b may use the color green to indicate interaction with the region of interest and the color red to indicate that the region of interest may not be interacted with by the percutaneous tool 108.

The patient chest motion model 435c is illustrated as a patient on a surgical table and is configured to show the movement of the patient's chest throughout the respiratory cycle. The patient chest motion model 435c will display a model of the patient's chest moving upwards during inhalation and downwards during exhalation. The patient chest motion model 435c allows a clinician to compare the other predictive metrics 435, each on display 104, while viewing the patient chest model 435c.

In addition, the plurality of the predictive metrics 435 may include drop down menus that allow a clinician to mark various target areas of the 3D model 412. As those skilled in the art will realize, the plurality of predictive metrics 435 and examples described herein are provided for illustrative purposes and are not intended to limit the scope of the present disclosure.

The indicator window 450 is a window that is configured to provide a clinician with procedure indicators, and is shown as including a probe indicator 452, a respiratory indicator 454, and a procedure indicator 456. The probe indicator 452 is configured to display a type of the percutaneous tool utilized during the surgical procedure. It is contemplated that each percutaneous tool 108 may include a tool identification that identifies the type of tool and its usage. Once the percutaneous tool 108 is coupled with the computing device 102, the tool identification may be utilized to update the probe indicator 452. As shown in FIGS. 4A-4C, the probe indicator 452 shows the percutaneous tool 108 as a percutaneous needle.

The respiratory indicator 454 indicates a phase of the respiratory cycle to which the image shown of the 3D model 412 corresponds. As shown in FIG. 4A, the respiratory indicator 354 indicates that the 3D model 412 shows the interior of the patient at full breath hold (i.e. absolute maximum inhalation). Respiratory indicator 454 further includes a pull-down button 454a which allows a clinician to select additional respiratory phases, such as inhalation, exhalation, and/or various points in-between. The pull-down button 454a allows a clinician to stop respiratory motion of the 3D model 412, thereby allowing the clinician to better view the locations of the region of interest indicator 416, the proposed location of the region of interest indicator 416p, the tool position indicator 414, and the proposed tool position indicator 416p. The procedure indicator 356 indicates the type of surgical procedure being performed, such as a biopsy, ablation, therapeutic treatment, or other similar percutaneous surgical procedure.

As shown in FIG. 4A, at full breath hold based on the location and entry angle of the percutaneous tool 108, the trajectory indicator 418 is shown as intersecting the region of interest indicator 416. However, because the patient's respiratory cycle continues during the surgical procedure, movement of the region of interest indicator 416 and tissue and/or other biological material 420 may cause the tool position indicator 414 (representing the percutaneous tool 108) to become incapable of reaching the region of interest indicator 416. FIGS. 4B and 4C illustrate this movement of the region of interest indicator 416 and tissue and/or other biological material 420, and show the suggested or proposed trajectories, as generated by computing device 102, that a clinician should follow to ensure interaction with the region of interest.

Referring now to FIGS. 4B and 4C, each of the model window 410, the predictive window 430 and the indicator window 450 are shown as described in the description of FIG. 4A. As indicated by the respiratory indicator 454, the 3D model 412 illustrates the current location of the tool position indicator 414 and the trajectory indicator 418 based on the angle and location of EM sensor 110. Further included within the model window 410 of FIG. 4B and FIG. 4C is the proposed location of the region of interest indicator 416p during the exhalation phase (FIG. 4B) and inhalation phase (FIG. 4C) of the respiratory cycle. The proposed tool position indicator 414p and the proposed trajectory indicator 418p show how the percutaneous tool 108 should be moved in order to interact with the proposed location of the region of interest indicator 416p. Although FIGS. 4B and 4C, show the 3D model 412 at the extremes of the exhalation and inhalation phases, respectively, it is contemplated that throughout the respiratory cycle from the exhalation phase through the inhalation phase, various dynamic views of the 3D model 412 smoothly transitions between the 3D model 412 shown in FIG. 4B and the 3D model 412 shown in FIG. 3C. Thus, the GUI 400 displays images of the 3D model 412 throughout the respiratory cycle, thereby allowing a clinician to better visualize the internal movement of the patient.

As shown in FIG. 4B, during the exhalation phase, the proposed region of interest indicator 416p has moved upwards 2 mm from the tool position indicator 414, as shown by the movement distance metric 435a of the predictive window 430. Based on the current angle and the location of the percutaneous tool 108, the tool position indicator 414 does not interact with the proposed location of the region of interest indicator 416p, as shown by the movement interaction metric 435b of the predictive window 430 displaying "NO." In order to interact with the proposed location of the region of interest indicator 416p, a clinician should either alter the location of the percutaneous tool 108 such that the tool position indicator 414 overlays the proposed location of the tool position indicator 414p and the trajectory indicator 418 overlays the proposed trajectory indicator 418p, or wait for the patient's respiratory cycle to proceed to a phase where the trajectory indicator 418 is shown as interacting with the region of interest 416.

Referring now to FIG. 4C, the 3D model 412 includes the proposed tool position indicator 414p, the proposed location of the region of interest indicator 416p, and the proposed trajectory indicator 418p. As shown in FIG. 4C, during the inhalation phase, the proposed location of the region of interest indicator 416p has moved downwards and is located about 5 mm from the full breath hold CT scan 3D model 412 of FIG. 4A, as shown by the movement distance metric 435a of predictive window 430. Based on the current angle and location of the percutaneous tool 108, the tool position indicator 414 does not interact with the proposed location of the region of interest indicator 416p, as shown by the movement interaction metric 435b of the predictive window 430. Thus, as the patient inhales, the proposed location of the region of interest indicator 416p approaches the full breath hold location of the region of interest indicator 416. Therefore, a clinician using the 3D model 412 shown in FIG. 4C would be able to determine that in order to reach the region of interest during the inhalation phase of the respiratory cycle, it is required to move the percutaneous tool 108 about 5 mm. Alternatively, the clinician may wait for the patient's respiratory cycle to proceed to a phase where the trajectory indicator 418 is shown as interacting with the region of interest 416.

Returning to FIG. 2 now, in an embodiment, the memory 202 may include one or more solid-state storage devices such as flash memory chips. Alternatively or in addition to the one or more solid-state storage devices, the memory 202 may include one or more mass storage devices connected to the processor 204 through a mass storage controller (not shown) and a communications bus (not shown). Although the description of computer-readable media included herein refers to a solid-state storage, it should be appreciated by those skilled in the art that computer-readable storage media may be any available media that may be accessed by the processor 204. That is, computer readable storage media includes non-transitory, volatile and non-volatile, removable and non-removable media implemented in any method or technology for storage of information such as computer-readable instructions, data structures, program modules, or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 102.

The processor 204 may be a general-purpose processor, a specialized graphics processing unit (GPU) configured to perform specific graphics processing tasks while freeing up the general-purpose processor to perform other tasks, and/or any number or combination of such processors. The display 206 may be touch sensitive and/or voice activated, enabling the display 206 to serve as both an input and output device. Alternatively, a keyboard (not shown), mouse (not shown), or other data input devices may be employed. The computing device 102 may receive CT image data of a patient from a server, for example, a hospital server, internet server, or other similar servers, for use during surgical planning. Patient CT image data may also be provided to the computing device 102 via a removable memory 202. The computing device 102 may receive updates to its software, for example, to the application 216, via a network interface 208. The computing device 102 may also display notifications on that display 206 that a software update is available.

The application 216 may be one or more software programs stored in the memory 202 and executed by the processor 204 of the computing device 102. As described above, during the planning phase, the application 216 guides a clinician through a series of steps to identify a target, size the target, size a treatment zone, and/or determine an access route to the target for later use during the procedure phase. In some embodiments, the application 216 is loaded on computing devices in an operating room or other facility where surgical procedures are performed, and is used as a plan or map to guide a clinician performing a surgical procedure, but without any feedback from the percutaneous tool 108 used in the procedure to indicate where the percutaneous tool 108 is located in relation to the plan. In other embodiments, the system 100 provides the computing device 102 with data regarding the location of the percutaneous tool 108 within the body of the patient, such as by EM tracking data, which the application 216 may then use to indicate on the plan and/or the 3D model 412 where the percutaneous tool 108 are located.

The application 216 may be installed directly on the computing device 102, or may be installed on another computer, for example a central server, and opened on the computing device 102 via the network interface 208. The application 216 may run natively on the computing device 102, as a web-based application, or any other format known to those skilled in the art. In some embodiments, the application 216 will be a single software program having all of the features and functionality described in the present disclosure. In other embodiments, the application 216 may be two or more distinct software programs providing various parts of these features and functionality. the application 216 communicates with a user interface module 218 that generates a graphical user interface for presenting visual interactive features to a clinician, for example, on the display 206, and for receiving clinician input, for example, via the input device 210. For example, the user interface module 218 may generate the GUI 400 of FIGS. 4A-4C and output the GUI 400 to the display 206 for viewing by a clinician.

The computing device 102 is linked to the display 104, thus enabling the computing device 102 to control the output on the display 104 along with the output on the display 206. The computing device 102 may control the display 104 to display output which is the same as or similar to the output displayed on the display 206. For example, the output on the display 206 may be mirrored on the display 104. Alternatively, the computing device 102 may control the display 104 to display different output from that displayed on the display 206. For example, the display 104 may be controlled to display guidance images and information during the procedure, while the display 206 is controlled to display other output, such as configuration or status information. The database 225 is illustrated as connectively coupled to the computing device 102 via the network interface 208. The database 225 may be located on a LAN consisting of a wired network and/or a wireless network, a WAN, a wireless mobile network, a BLUETOOTH® network, and/or the internet. As used herein, the term "clinician" refers to any medical professional (i.e., doctor, surgeon, nurse, or the like) or other user of the system 100 involved in planning, performing, monitoring and/or supervising a medical procedure involving the use of the embodiments described herein.

Detailed embodiments of devices and systems incorporating such devices, and methods using the same, have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to employ the present disclosure in virtually any appropriately detailed structure.

What is claimed is:

1. A system for navigating to and interacting with a region of interest during a respiratory cycle of a patient, the system comprising:
   a percutaneous tool including a tool sensor, the percutaneous tool configured for insertion into an interior of a patient and interaction with a region of interest during a surgical procedure;
   an electromagnetic (EM) tracking system including:
      an EM field generator configured to generate an EM field;
      a plurality of patient sensors disposed on the patient and movable within the EM field; and
      a tracking module configured to determine location and motion data corresponding to the plurality of patient sensors and the tool sensor within the EM field;
   a display device; and
   a computing device including:
      at least one processor; and
      a memory storing instructions which, when executed by the at least one processor, cause the computing device to:
         receive a plurality of images of the patient's body;
         receive the location and motion data determined by the tracking module;
         generate a three-dimensional (3D) model of at least a portion of the interior of the patient based on the plurality of images;
         correlate a location of the plurality of patient sensors within the EM field at a maximum inhalation point and a location of the plurality of patient sensors within the EM field at a maximum exhalation point to the plurality of images;
         predict movement of the interior of the patient, the percutaneous tool, and the region of interest throughout the respiratory cycle based on the correlation between the location of the plurality of patient sensors within the EM field at the maximum inhalation point and the location of the plurality of patient sensors within the EM field at the maximum exhalation point to the plurality of images; and
         cause the display device to display a graphical user interface (GUI) including:
            a model window for displaying a rendering of the 3D model generated depicting movement of the interior of the patient, the percutaneous tool, and the region of interest throughout the respiratory cycle, wherein the rendering is user-manipulatable to display selective tissue, organs, or bones within the region of interest; and
            a user-selectable button enabling a user to select a phase of the respiratory cycle and configured to stop movement of the rendering and display an image of the plurality of images of the patient's body associated with the phase selected.

2. The system according to claim 1, wherein the respiratory cycle is divided into an inhalation phase and an exhalation phase, and each image of the plurality of images correspond to either the inhalation phase or the exhalation phase.

3. The system according to claim 2, wherein the instructions, when executed by the at least one processor, further cause the computing device to predict movement of the interior of the patient and the region of interest throughout the respiratory cycle based on the location and motion data of the plurality of patient sensors and the 3D model of the interior of the patient.

4. The system according to claim 3, wherein the instructions, when executed by the at least one processor, further cause the computing device to predict movement of the percutaneous tool based on the predicted movement of the interior of the patient and the location and motion data of the tool sensor.

5. The system according to claim 1, wherein the model window is further configured to display a trajectory of the percutaneous tool.

6. The system according to claim 5, wherein the model window is further configured to display:
   a proposed trajectory of the percutaneous tool throughout the respiratory cycle; and
   a proposed location of the region of interest throughout the respiratory cycle.

7. The system according to claim 6, wherein the proposed trajectory of the percutaneous tool and the proposed location of the region of interest change throughout the respiratory cycle.

8. The system according to claim 6, wherein the instructions, when executed by the at least one processor, further cause the computing device to determine interaction with the region of interest if the trajectory of the percutaneous tool is closely matched with the proposed trajectory of the percutaneous tool.

9. The system according to claim 6, wherein the instructions, when executed by the at least one processor, further cause the computing device to determine interaction with the region of interest based on the trajectory of the percutaneous tool, the proposed trajectory of the percutaneous tool, and the proposed location of the region of interest.

10. The system according to claim 1, wherein the GUI window further includes:
    a predictive window configured to display a plurality of predictive metrics.

11. The system according to claim 10, wherein the predictive metrics include one or more of:
    patient chest motion during respiration,
    a distance of movement of the region of interest during respiration, and
    an indication of interaction with the region of interest.

12. The system according to claim 1, wherein the GUI window further includes:
    an indicator window configured to display:
       a tool indicator,
       a respiratory indicator, and
       a procedure indicator,
    wherein the tool indicator indicates a type of tool being used during the surgical procedure, the respiratory indicator indicates a phase of the respiratory cycle, and the procedure indicator indicates a type of the surgical procedure.

13. The system according to claim 1, wherein the percutaneous tool is selected from the group consisting of:
    an aspiration needle,
    an access tool,
    a biopsy tool, and
    an ablation tool.

14. A method for navigating to and interacting with a region of interest during a respiratory cycle of a patient, the method comprising:
    receiving a plurality of images of a patient's body;
    generating a three-dimensional (3D) model of at least a portion of an interior of the patient's body and a 3D model of a region of interest based on the plurality of images;
    detecting a position of a percutaneous tool inserted into the interior of the patient based on a tool sensor coupled to the percutaneous tool;
    obtaining location and motion data corresponding to the tool sensor and a plurality of sensors disposed on the patient within an electromagnetic (EM) field generated by an EM tracking system;
    correlating a location of the plurality of patient sensors within the EM field at a maximum inhalation point and a location of the plurality of patient sensors within the EM field at a maximum exhalation point to the plurality of images;
    predicting movement of the interior of the patient, the percutaneous tool, and the region of interest based on the correlation between the location of the plurality of patient sensors within the EM field at the maximum inhalation point and the location of the plurality of patient sensors within the EM field at the maximum exhalation point to the plurality of images; and
    displaying a graphical user interface (GUI), the GUI including:
       a model window configured to display a view of the 3D model of the interior of the patient, the percutaneous tool, the region of interest, and a rendering depicting the predicted movement of the interior of the patient, the percutaneous tool, and the region of interest throughout the respiratory cycle, wherein the rendering is user-manipulatable to display selective tissue, organs, or bones within the region of interest; and
       a user-selectable button enabling a user to select a phase of the respiratory cycle and configured to stop movement of the rendering and display an image of the plurality of images of the patient's body associated with the phase selected.

15. The method according to claim 14, wherein predicting movement of the interior of the patient and the region of interest is based on the location and motion data of the plurality of sensors and the 3D model.

16. The method according to claim 14, wherein the GUI further includes an indicator window configured to display a tool indictor, a respiratory cycle indicator, and a procedure indicator,
    wherein the tool indictor indicates a type of tool being used during a surgical procedure, the respiratory cycle indicator indicates a position within a respiratory cycle, and the procedure indicator indicates a type of the surgical procedure.

17. The method according to claim 14, wherein the model window is further configured to display:
    a trajectory of the percutaneous tool;
    a proposed trajectory of the percutaneous tool throughout the respiratory cycle; and
    a proposed location of the region of interest throughout the respiratory cycle.

18. The method according to claim 17, wherein the proposed trajectory of the percutaneous tool and the proposed location of the region of interest change throughout the respiratory cycle.

19. The method according to claim 17, further comprising determining interaction with the region of interest based on the trajectory of the percutaneous tool, the proposed trajectory of the percutaneous tool, and the proposed location of the region of interest.

* * * * *